(12) United States Patent
Hatajima et al.

(10) Patent No.: US 6,335,468 B1
(45) Date of Patent: Jan. 1, 2002

(54) PROCESS FOR PRODUCTION N-ACYL AMINO ACID AMIDE

(75) Inventors: Toshihiko Hatajima; Tatsuru Tabohashi, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/676,988

(22) Filed: Oct. 2, 2000

(30) Foreign Application Priority Data

Oct. 20, 1999  (JP) ............................................. 11-297792

(51) Int. Cl.$^7$ ............................................. C07C 231/02
(52) U.S. Cl. ..................... 564/133; 564/136; 564/138; 564/153; 564/155; 564/159; 546/189
(58) Field of Search .......................... 546/189; 564/133, 564/136, 138, 153, 155, 157

(56) References Cited

FOREIGN PATENT DOCUMENTS

JP          61-000050         1/1986

*Primary Examiner*—Johann Richter
*Assistant Examiner*—Brian J. Davis
(74) *Attorney, Agent, or Firm*—Oblon, Spivak, McClelland, Maier & Neustadt, P.C.

(57) ABSTRACT

There is provided a process for producing an N-acyl amino acid amide, comprising a condensation reaction of an N-acyl amino acid with an amine and/or an ammonia, preferably a primary amine, a secondary amine and/or an ammonia under dehydration in the presence of a boron compound as the catalyst under coexistence of an alcohol as the auxiliary solvent, at a high yield for a short time. A medium for hylotropic dehydration such as hydrocarbon compounds may be used in the reaction.

29 Claims, No Drawings

PROCESS FOR PRODUCTION N-ACYL AMINO ACID AMIDE

BACKGROUND OF THE INVENTION

1. Field of the Invention

The present invention relates to an improved process for the production of N-acyl amino acid amide.

The N-acyl amino acid amide is employed for use application, such as an anti-oxidant, an additive agent for cosmetic preparations, an antistatic additive and an antimicrobial agent as an oil soluble nonionic surface active agent which is low toxic, low skin irritate and excellent in biodegradability. And, also it has a faculty or function to solidify an organic medium liquid at room temperature, in particular an inflammable organic medium, such as natural type of and synthetic type of mineral oils and animal and vegetable oils, and a nonflammable organic phosphorus compound and organochlorine based compound to the gel form, the agar gel form or the block form (Refer to Japanese Patent Kokoku Publications JP-B-51-42079, JP-B-53-13434 and JP-B-53-27776.), and therefore its industrial utility value in the gelatinizing agent for oils is noticed and watched.

DESCRIPTION OF THE RELATED ART

As the process for the production of N-acyl amino acid amide, the process for converting the carboxyl group in the N-acyl amino acid into an active group of high reactivity, such as that in an ester, an acid halide and an acid anhydride, and then reacting the thus obtained derivative thereof with an amine, the process for heating an N-acyl amino acid with an amine under dehydration to form an amide directly, and the like are known.

For the process for converting the N-acyl amino acid to an activated carboxylic acid derivative of which the carboxyl group has been converted into an active group of high reactivity, there are many descriptions in the literatures and the like, and therefore the suitable derivative can be selected by considering the reactivity of the N-acyl amino acid used as the starting material and the stability of the derivative obtained, and further in order to produce an objective N-acyl amino acid amide, it is essential to obtain the activated carboxylic acid derivative of the reaction intermediate at a high yield. For example, N-acyl amino acid ester can be produced in the condensation reaction under dehydration between an N-acyl amino acid and an alcohol, and however in order to obtain the N-acyl amino acid ester at a high yield, it is necessary to shift the equilibrium in the reaction by using the alcohol in a much excessive amount thereto, removing the water produced in the reaction, or the like, because the reaction is a typical equilibrium reaction. For one example therefor, the process for obtaining N-lauroyl-L-glutamic acid dimethy ester quantitatively in the reaction of N-lauroyl-L-glutamic acid with methanol in the presence of an acid catalyst using trimethyl orthoformate as the dehydrating agent is disclosed (Refer to Japanese Patent Kokai Publication JP-A-9-221461.), and further the process for producing N-lauroyl-L-glutamic acid di-n-butyl amide in the reaction of N-lauroyl-L-glutamic acid dimethyl ester with n-butylamine through an ester-amide exchange reaction is disclosed (Refer to Japanese Patent Kokai Publication JP-A-10-001463.). In the said process wherein an activated N-acyl amino acid derivative is produced as a reaction intermediate on route, the reaction proceeds with comparatively moderate condition and gives a good yield. And however, it has many reaction steps and burdensome in operations therefor, and therefore is disadvantageous in productivity as compared with the process for directly producing an amide (a direct amidation process), because it is necessary to remove surplus reaction solvent and dehydrating agent which have been used for the production of the reaction intermediate before proceeding to the amidation process. And, also there is a problem that 3 to 6 moles of the amine in surplus are necessarily used per 1 mole of the ester in order to carry out the amidation reaction smoothly.

As an example of the process for a direct amidation by heating a N-acyl amino acid with an amine to remove water, the process for obtaining N-acyl amino acid amide by heating directly N-acyl amino acid having acyl group(s) in the carbon number of 1 to 22 with an alkylamine in the carbon number of 8 or more, or the like to react them is known (Refer to Japanese Patent Kokoku Publication JP-B-52-18691.), and however, the process is difficult to be applied to the case where the alkylamine is one in the carbon number of 7 or less or an ammonia. That is, such known process corresponds to the process for obtaining an objective N-acyl amino acid amide which comprises mixing a N-acyl amino acid with an amine in the carbon number of 8 or more, and heating them directly at the temperature of 160 to 200° C. or heating them under reflux to remove water (dehydration) in the presence of an inactive solvent, such as xylene, and however the process has the following weak points (shortcomings). When the process is applied to the alkyl amine in the carbon number of 7 or less, or the like, the amine flies off under the condition of direct heating at the temperature of 160 to 200° C. or under the condition of heating in the presence of xylene or the like, because the boiling point of the amine is low, and therefore, the reaction yield is lowered. And, in the case where an amino acid residue in the N-acyl amino acid is one in the acidic amino acid and it has plural (two or more) carboxyl groups, the tendencies that one carboxyl group is easy to react, and on the other hand the other one is lowered in reactivity, are marked. To this end, in order to obtain a di- or tri-amide substitution derivative, they are reacted necessarily under a cruel (harsh) condition of a high temperature and a long time. Under such reaction condition, in addition to the condensation reaction between the objective carboxyl group and the amine, there are produced the secondary reactions, such as oxidation of the amine, an exchange reaction under condensation between an N-acyl group thereof and an amine, and a formation of nitrile to cause preparation of by-products (arisings). And, in the case where an optically active N-acyl amino acid is used as the starting material, because a racemization proceeds simultaneously, there are caused a problem that an objective optically active N-acyl amino acid amide is not obtained, and the like problem.

In order to improve the shortcomings (weak point) as described above, in a process for direct amidation of an N-acyl amino acid with a primary amine or an ammonia, the process wherein a boron compound as the catalyst coexists in the reaction thereof is disclosed (Refer to Japanese Patent Kokai Publication JP-A-61-00050.). By placing the catalyst coexistent, the reaction can be carried out at a low temperature and further the desired (objective) product can be obtained at a high yield as compared with the reaction without the catalyst. Moreover, since the reaction is carried out at a low temperature, the effects that a racemization is kept down and the like are obtained, even though an optically active N-acyl amino acid may be used as the starting material. However, the catalyst used in the reaction is soluble in water, and thus in the case where the reaction is carried out without a medium or in the hydrocarbon compound which is a medium for hylotropic (azeotropic)

dehydration or a mixture thereof coexistent, the catalyst is not dissolved completely to give a system of the reaction heterogeneous, and the thus insoluble catalyst is deposited to the wall inside the reactor as scale buildup to account for (cause) bumping or the like. In addition, there is a problem that the reaction can not be accelerated and therefore a reaction time can not be shortened, because the insoluble catalyst can not be concerned with the reaction to lower the catalyst efficiency, while the amount of the catalyst added thereto is limited. And, in the reaction of an N-acyl amino acid with a secondary amine, according to such above process, the reactivity of the secondary amine is not accelerated sufficiently, and therefore the reaction does not proceed smoothly. As a result, the yield of the thus obtained N-acyl amino acid amide was unsatisfactory.

SUMMARY OF THE INVENTION

1. Problems to be solved by the Invention

Under the background of the related art described above, the problem to be solved by the present invention is to develop, in a process for producing N-acyl amino acid amide comprising the step of reacting directly an N-acyl amino acid with a primary amine, a secondary amine or an ammonia, there is developed an improved process to solve the problem in the production process, such as the deposition of the catalyst (the scale buildup of the catalyst) and the like, and moreover to enhance the catalyst efficiency so that the reaction may proceed for a short time and at the same time the objective product can be obtained at a good yield.

2. Means to solve Problems

In order to solve the problems, the present inventors have eagerly studied and as a result found that by reacting an N-acyl amino acid with a primary amine, a secondary amine or an ammonia in the presence of a boron compound as the catalyst with an alcohol coexistent as the auxiliary (assistant) solvent, the system of reaction can be made homogeneous, even in the presence of the hydrocarbon compound which is a medium for hylotropic (azeotropic) dehydration or a mixture thereof, or even without the medium for hylotropic dehydration (the hydrocarbon compound or the mixture thereof), and therefore the problems in the production process can be improved, for example, the scale buildup of the catalyst to the wall inside the reactor can be suppressed. In addition, they have found that by making the catalyst homogeneous in the system of reaction, the catalyst efficiency can be enhanced to accelerate the reaction and the N-acyl amino acid amide is obtained at a good yield for a short time, as compared with the system of the boron compound as the catalyst alone (without using the auxiliary solvent).

These above findings have led to the completion of the present invention.

That is to say, the present invention is directed to, in a process for producing an N-acyl amino acid amide comprising a condensation reaction of an N-acyl amino acid with amine and/or ammonia, and preferably a primary amine, a secondary amine or an ammonia under dehydration, an improved process wherein said condensation reaction is conducted (performed) in the presence of a boron compound as the catalyst with an alcohol coexistent as the auxiliary solvent. The N-acyl amino acid may be in the salt form.

A process for producing an N-acyl amino acid amide, comprising a condensation reaction of an N-acyl amino acid with amine and/or ammonia, and preferably a primary amine, a secondary amine or an ammonia under dehydration in the presence of a boron compound as the catalyst under coexistence of at least one alcohol as the auxiliary solvent, is also contained in the present invention.

The N-acyl amino acid may be in the salt form.

In the present invention, the condensation reaction is conducted (performed) preferably in the acidic condition. In such case, the N-acyl amino acid may be in the free form.

PREFERRED EMBODIMENTS OF THE INVENTION

For the process for producing an N-acyl amino acid amide comprising a condensation reaction of an N-acyl amino acid with a primary amine, a secondary amine or an ammonia under dehydration, the known process, known means, known operations and the like therefor as well as developed ones therefor are employed, without the use of the auxiliary solvent as the constitution of the present invention. Accordingly, the whole contents of the publications on the process for reaction of an N-acyl amino acid with a primary amine, a secondary amine or an ammonia under dehydration to produce an N-acyl amino acid amide, are incorporated therein by reference.

For an amino acid as the component (ingredient) constituting the N-acyl amino acid used as the starting material in the present invention, any one of an acidic amino acid, a neutral amino acid and a basic amino acid maybe employed, and also any one of an α-amino acid, a β-amino acid and an ε-amino acid may be employed. For example, glycine, β-alanine, α-alanine, valine, leucine, phenylalanine, 3,4-dioxyphenylalanine, serine, threonine, methionine, lysine, ornithine, arginine, histidine, ε-aminocaproic acid, glutamic acid, aspartic acid and the like are shown. The N-acyl amino acid may be in the salt form. For example, N-acyl glutamic acid disodium salt, N-acyl glutamic acid monosodium salt, etc. may be employed. Among them, the mono salt thereof is preferable, since it is easy to obtain. In this invention, hereinafter the N-acyl amino acid includes that in the salt form.

For an acyl as the component constituting the acyl group thereof, an acyl group which can be or may be derived from a straight chain or branched chain, saturated or unsaturated fatty acid in the carbon number of 1 to 30 may be employed. For example, an acyl group from a single fatty acid, such as formyl, acetyl, propionyl, caproyl, capryloyl, caprinoyl, lauroyl, myristoyl, palmitoyl, stearoyl, behenoyl, oleoyl, linoleoyl, and an acyl group (acyl groups) from a natural type of mixed fatty acid(s), such as an acyl from a coconut oil fatty acid, an acyl from a hardened beef tallow fatty acid and the like, and in addition an acyl from an aromatic carboxylic acid, such as an acyl from a benzoic acid and the like are shown. Of course, such acyl group can be derived from a law material other than such fatty acid.

For the amine to be reacted with the N-acyl amino acid while heating, a straight chain or branched chain, saturated or unsaturated, primary and secondary amine, including mono-or di-alcohol amine, aromatic amine, alicyclic amine, etc. in the carbon number of 1 to 60, and the like are cited (exemplified). For example, methylamine, ethylamine, propylamine, butylamine, hexylamine, octylamine, 2-ethylhexylamine, laurylamine, cetylamine, stearylamine, cycopentylamine, cyclohexylamine, 4-isopropylcyclohexylamine, aniline, benzylamine, naphthylamine, 4-isopropylaniline, dimethylamine, N-methylethylamine, diethylamine, di-n-propylamine, di-n-butylamine, N-methylbutylamine, piperidine, 3,5-dimethylpiperidine, N-methyldodecylamine, dilaurylamine, distearylamine, N-methylbenzylamine, monoethanolamine, diethanolamine, and the like can be specifically shown.

For the boron compound used as the catalyst, an orthoboric acid, a metaboric acid, a pyroboric acid and a boric oxide (boron oxide) and the like are suitable, and any one compound alone or more compounds in combination as selected among them may be used in the present invention. And, it has no objection anything that a borate (borate salt), such as borax (pyroborate), ammonium borate (ammonium pentaborate) and the like, may be used in the neutralization form with an inorganic acid, such as sulfuric acid, hydrochloric acid, nitric acid, phosphoric acid and the like.

For the alcohol used as the auxiliary solvent coexistent in the system of reaction, a straight chain, branched chain, saturated or unsaturated, aliphatic alcohol (fatty alcohol) in the carbon number of 3 to 8, a saturated or unsaturated cyclic alcohol in the carbon number of 3 to 8, a saturated or unsaturated alkyl ether alcohol (including an alkenyl ether alcohol etc.), and the like are suitable.

For the straight chain, branched chain, saturated or unsaturated aliphatic alcohol in the carbon number of 3 to 8, for example, 1-propanol, 2-propanol, 1-butanol, 2-butanol, 2-methyl-i-propanol, tert-butanol, 1-pentanol, 2-methyl-1-butanol, 4-methyl-1-butanol, 2-methyl-2-butanol, 1-hexanol, 1-heptanol, 1-octanol, 2-ethylhexanol, allyl alcohol, crotyl alcohol, methylvinyl carbinol and the like are shown specifically. For the saturated or unsaturated cyclic alcohol in the carbon number of 3 to 8, for example, cyclopentanol, cyclohexanol and the like. For the saturated or unsaturated alkyl ether alcohol, for example, which is represented by the following general formula (1):

$$R^1 \text{—O—} R^2 \text{—OH} \tag{1}$$

wherein $R^1$ denotes a straight (linear) chain or branched chain, alkyl group or unsaturated hydrocarbon radical (including alkenyl group, etc.) in the number of carbon atoms 1 to 4, and $R^2$ denotes a straight chain or branched chain alkyl group in the number of carbon atoms 2 to 5, specifically 2-methoxy ethanol, 2-ethoxy ethanol, 2-propoxy ethanol, 2-isopropoxy ethanol, 2-butoxy ethanol, 1-methoxy-2-propanol, 1-ethoxy-2-propanol, 3-ethoxy-1-propanol, 1-propoxy-2-propanol, 1-tert-butoxy-2-propanol, 1-methoxy-2-butanol, 3-methoxy-1-butanol, 3-methoxy-3-methyl-1-butanol, ethylene glycol vinyl ether, ethylene glycol allyl ether, propylene glycol vinyl ether, propylene glycol allyl ether and the like are shown. Any one compound alone or plural compounds mixed selected from the above compounds may be used.

In the case where the auxiliary (assistant) solvent does not coexist in the system of reaction, since the catalyst of the boron compound is not dissolved completely, and therefore the system of reaction is heterogeneous, the reaction efficiency is low, and in addition the insoluble catalyst is deposited to the wall inside the reactor as scale buildup. As a result, particularly in the early stage of the reaction, an amount of the dehydrated water, which is produced in the condensation reaction, is much, and it may give rise to bumping, bubbling (foaming), and the like, because it shows a tendency to increase a viscosity (viscidity).

On the other hand, in the case where the auxiliary solvent coexists in the presence of the boron compound as the catalyst, the system of reaction is made homogeneous to improve the reaction efficiency. Moreover, an amount of the catalyst to be added can be increased to accelerate the reaction remarkably and to shorten the reaction time, as compared with the case using the catalyst of the boron compound alone. And, the N-acyl amino acid and the amine unstable to heat, may not give rise to a secondary reaction such as decomposition, the objective dehydration reaction may proceed, and therefore the objective N-acyl amino acid amide can be obtained at a good yield. Further, there is no caused scale buidup of the catalyst to the wall inside the reactor, and thus there is no care from bumping, foaming, and the like on the production process. Even though an optically active N-acyl amino acid may be used as the starting material, the reaction is completed for a short time at the reaction temperature of approximately 110 to 125° C., and therefore the racemization does not arise whereby the objective optically active N-acyl amino acid amide can be obtained.

In carrying out the present invention, an N-acyl amino acid, and an amine or an ammonia are allowed to coexist together, and further a boron compound and the auxiliary solvent are added in small quantities thereto, and then the resulting mixture may be only heated in the presence of the medium for hylotropic (azeotropic) dehydration, or without the medium for azeotropic dehydration. Accordingly, the operation for reaction is much easier. Of course, in addition to the auxiliary solvent, the other solvent(s), which does not cause harm to the effects obtained in the present invention, may be employed for the present invention, with or without such medium for azeotropic dehydration.

Accordingly, for the medium used in the present invention, the auxiliary solvent is essential, the medium for azeotropic dehydration may be employed or may not be employed, and in addition, the other solvent(s) as described above may be employed or not.

Regarding the ratio of the N-acyl amino acid and the amine employed as the starting materials, 1.0 equivalence or more of the amine can be used per 1 equivalence of the carboxyl group in the N-acyl amino acid without further special limitation may be employed, and naturally, preferably 1.0 to 3.0, more preferably 1.0 to 1.5 equivalence of the amine can be used per 1 equivalence of the carboxyl group in the N-acyl amino acid. That is, for the amine consumed in the reaction, one equivalence of the amine corresponds to one equivalence of the carboxyl group therein, and however, as the reaction proceeds, since a concentration of the free amine is lowered, the amine may be preferably used in a slightly excessive amount under the economically advantageous range thereof to avoid a long time requirement for completion of the reaction. In the case where the amine is any one of a methylamine, an ethylamine or the like and an ammonia may be reacted therewith, because any of these amines or an ammonia is a substance having a very low boiling point, the substance tends to fly off easily from the system of reaction under heating, and therefore it is preferable to increase much the equivalence ratio of the amine or the ammonia per the carboxyl group in the N-acyl amino acid as the starting materials. That is, it is preferable to fill (compensate) the amine in the gas state or the ammonia gas, little by little under the proceeding of reaction so that the equivalence ratio of such low boiling point of amine or the ammonia per the remaining carboxyl group in the system of reaction may be allowed to be 1.0 or more.

An amount for addition of the boron compound used as the catalyst is not limited particularly, and it is preferable to add 0.1 to 10 equivalences of the substance (the boron compound) to 1 equivalence of the carboxyl group in the N-acyl amino acid. That is, in the case where less than 0.1 equivalence of the substance thereto may be added, the effect to accelerate the reaction as the catalyst is not given sufficient, and in the case where more than 10 equivalences thereof thereto may be added, a remarkable effect is not expected because the function or capacity of the catalyst gets nearly to saturation.

An amount for addition of the alcohol used as the auxiliary (assistant) solvent is not limited particularly, and it is preferable to add the alcohol in the 0.1 to 10 times by weight as much as the catalyst of boron compound used. That is, for reasons to employ the alcohol in such range, in the case where less than 0.1 time of the alcohol by weight thereto is added, it is not sufficient to make the system of reaction homogeneous, and in the case where more than 10 times of the alcohol by weight thereto is added, it may tend to become easily disadvantageous in the operation for removing the same (alcohol) after the completion of the reaction.

For the heating temperature in the reaction, in the case where no medium (solvent) for azeotropic dehydration may be used, it is generally preferable to employ the temperature for heating of 100° C. or higher to remove the water produced in the reaction, and as the temperature for heating grows higher, while the reaction may be accelerated, it is particularly preferable to employ the temperature of 110 to 150° C. to suppress the secondary reactions. Further, in the case where the optically active N-acyl amino acid amide is obtained, it is most preferable to employ the temperature of 110 to 125° C. to suppress the racemization. The reaction without placing the medium for azeotropic dehydration, is preferable in the case where an amine in the carbon number of 8 or more may be employed, and in the case where an amine in the carbon number of less than 8 or ammonia may be used, it is necessary to exercise ingenuity for the device or the like, because an operability of stirring and the like may tend to be easily lowered.

On the other hand, the process for carrying out a heating reaction under the coexistence of a medium for azeotropic dehydration, since the water produced in the reaction may be easily removed out of the system of reaction through azeotropic distillation, is suitable also even in the case where an amine in the carbon number of less than 8 as the starting material may be employed. For the medium for azeotropic dehydration, any one which does not react with the N-acyl amino acid, or the amine or ammonia as the starting material can be selected without further special limitations.

A hydrocarbon compound is most preferable, because the washing with water, or an acid or alkaline aqueous solution using preparation of the phases separated after completion of the reaction, can be easily effected. As the medium for azeotropic distillation, the hydrocarbon compound in the boiling point of 98 to 150

20 C. is desired. That is, for the reasons to such suitable temperature range employed, in the case of the hydrocarbon compound in the boiling point of lower than 98° C., the temperature for the system of reaction is too low to get the velocity of reaction sufficiently, and also in the case of the hydrocarbon compound in the boiling point of higher than 150° C., while the reaction may proceed without delay (in short order), undesirable secondary reactions, such as decomposition of the N-acyl amino acid, oxidation of the amine, and the like may proceed. For examples of the medium for azeotropic dehydration, heptane, isooctane, methylcyclohexane, cycloheptane, methylcyclohexene, diisobutylene, toluene, xylene, octane, octene, dimethylcyclohexane, trimethylcyclohexane, and the like can be shown. When it is necessary to suppress particularly the racemization, the hydrocarbon compound in the boiling point of 98 to 125° C. is most desired for the medium for azeotropic distillation (dehydration), and the examples therefor include preferably the compound, such as heptane, isooctane, methylcyclohexane, cycloheptane, methylcyclohexene, diisobutylene, toluene, octane, octene and dimethylcyclohexane, and the mixture thereof, and the mixture obtained by mixing properly the one or more compounds exemplified above for the hydrocarbon compound with one or more hydrocarbon compounds having a high boiling point such as xylene so that the boiling point of the obtained mixture may be adjusted to 125° C. or lower.

After completion of the reaction, for the process to isolate the objective (desired) N-acyl amino acid amide, for example, in the case where the medium for azeotropic dehydration is not used in the reaction, the product is dissolved while heating in an organic solvent, such as ethyl acetate, after the reaction, and the catalyst, unreacted starting material (8) and/or the secondary reaction product(s) are extracted with a water, or an acid or alkaline aqueous solution or the like to remove, and then the resulting material can be subjected to the recrystallization process under cooling to obtain an objective N-acyl amino acid amide. According to the kind of the N-acyl amino acid amide, it may make in many cases not only oils but also organic solvent(s), such as ethyl acetate, gelation (gel formation), and in this case, since at the time of cooling a crystallization may not arise and the whole mass is made to gelation, by repeating the washing up of the reaction composition with a water, or an acid or alkaline aqueous solution in the slurry state, the catalyst, the unreacted starting material(s) and/or the secondary reaction product(s) (by-product(s)) can be removed, whereby the objective N-acyl amino acid amide can be obtained.

In the case where the hydrocarbon compound may be used as the medium for azeotropic dehydration, after the end of the reaction, the medium for azeotropic dehydration is removed by distillation, and then the process for recrystallization thereof from the organic solvent, such as ethyl acetate, as described above can be employed. In addition, by using the property that the objective N-acyl amino acid amide is difficult to be dissolved in a water, the process described in the PCT Publication WO98-08806, e.g., the process for an extraction with an acid and/or an extraction with an alkali may be performed whereby the catalyst, the unreacted starting material(s), the secondary reaction product(s) and/or the like can be extracted and removed. After that, by effecting substitution of the solvents from the organic medium to the water through azeotropic distillation to precipitate the objective product in the granulated solid state. According to the thus described processes or the like, the objective and desired N-acyl amino acid amide can be obtained.

The whole content of the Japanese application serial No. 297792/1999 filed on Oct. 20, 1999, upon which the priority is claimed for this application, is incorporated in the specification of this application:

EXAMPLES

The present invention is illustrated specifically by referring to the following examples. And, however the present invention is not limited to these examples.

EXAMPLE 1

A 2L-flask equipped with a stirrer, an H-shaped tube having a device for reflux, a dropping instrument and a thermometer was arranged for a reactor and air in the reactor was replaced by nitrogen gas. 52.2 g of boric oxide (boron oxide), 480 g of toluene, 111.1 g of 1-butanol and 137.2 g of n-butylamine were introduced to the flask, and then 49.5 g of 95% sulfuric acid aqueous solution was added thereto drop by drop at 70° C. or lower in the liquid temperature. Subsequently, 267 g of N-lauroyl-L-glutamic acid sodium salt ("AMISOFT LS-11", manufactured by Ajinomoto Co., Inc.) was added thereto carefully, and a reaction for azeotropic (hylotropic) dehydration was conducted under nitrogen atmosphere for 10 hours to remove the water produced by heating the mixture under reflux. After confirming the fact that the reaction was completed by the HPLC (high performance liquid chromatography), 600 g of hot water was added to the reaction solution, and 18.6 g of 95% sulfuric acid aqueous solution was added thereto, and the resulting solution was stirred for 15 minutes at 80° C. and then allowed to stand for 10 minutes at the same temperature. After confirming the fact that a pH value of the water layer was 3 or less, the water layer was removed. Further, 600 g of 1% sulfuric acid aqueous solution was added to the remaining organic layer, and the step for extraction with an acid was conducted in the same manner as above. Next, 600 g of hot water, 75 g of 27% sodium hydroxide aqueous solution and 27 g of sodium chloride were added thereto, and the resulting solution was stirred for 15 minutes at 80° C. and then allowed to stand for 1 hour at the same temperature, and then the water layer was removed. This step for extraction with an alkali was repeated further once again. 900 g of hot water was added to the remaining organic layer and the solution was neutralized to adjust the pH value of the water layer to 7 or the value in the neighborhood thereto. The organic solvent was removed through azeotropic distillation. The granulated solid material thus obtained was collected by filtration and dried under reduced pressure to obtain the reaction product (310 g). A purity of the obtained N-lauroyl-L-glutamic acid di-n-butyl amide was 95% in the determination of the purity by HPLC.

EXAMPLE 2

A 2L-flask equipped with a stirrer, an H-shaped tube having a device for reflux, a dropping instrument and a thermometer was arranged for a reactor and air in the reactor was replaced by nitrogen gas. 143 g of borax, 480 g of toluene and 111.1 g of 1-butanol were introduced to the flask, and then 38.7 g of 95% sulfuric acid aqueous solution was added thereto drop by drop. Subsequently, 137.2 g of n-butyl amine and 247 g of N-lauroyl-L-glutamic acid ("AMISOFT LA", manufactured by Ajinomoto Co., Inc.) were added thereto carefully, and a reaction for azeotropic dehydration was conducted under nitrogen atmosphere for 10 hours to remove the water produced by heating the mixture under reflux. After the end of the reaction, the treatment was conducted in the same manner and operation as those in the example 1 to obtain the reaction product (317 g). A purity of the obtained N-lauroyl-L-glutamic acid di-n-butyl amide was 96% in the determination of the purity by HPLC.

EXAMPLE 3

A 2L-flask equipped with a stirrer, an H-shaped tube having a device for ref lux, a dropping instrument and a thermometer was arranged for a reactor and air in the reactor was replaced by nitrogen gas. 52.2 g of of boric oxide, 247 g of N-lauroyl-L-glutamic acid ("AMISOFT LA", manufactured by Ajinomoto Co. , Inc.), 480 g of toluene, 125 g of 1-ethoxy-2-propanol and 137.2 g of n-butylamine were introduced to the flask, and a reaction for azeotropic dehydration was conducted under nitrogen atmosphere for 10 hours to remove the water produced by heating the mixture under reflux.

After the end of the reaction, a treatment for the reaction mixture was conducted in the same manner and operation as those in the example 1 to obtain the reaction product (320 g). A purity of the obtained N-lauroyl-L-glutamic acid di-n-butyl amide was 96% in the determination of the purity by HPLC.

EXAMPLE 4

A 2L-flask equipped with a stirrer, an H-shaped tube having a device for reflux, a dropping instrument and a thermometer was arranged for a reactor and air in the reactor was replaced by nitrogen gas. 26.1 g of boric oxide, 266 g of N-palmitoyl-L-valine, 480 g of toluene, 55.6 g of 1-butanol and 121 g of n-octylamine were introduced to the flask, and a reaction for azeotropic dehydration was conducted under nitrogen atmosphere for 9 hours to remove the water produced by heating the mixture under reflux.

After the end of the reaction, the treatment for the reaction mixture was conducted in the same manner and operation as those in the example 1 to obtain the reaction product of N-palmitoyl-L-valine-n-octyl amide (318 g). A purity of the obtained N-palmitoyl-L-valine-n-octyl amide was 98% in the determination of the purity by HPLC.

EXAMPLE 5

A 2L-flask equipped with a stirrer, an H-shaped tube having a device for reflux, a dropping instrument and a thermometer was arranged for a reactor and air in the reactor was replaced by nitrogen gas. 26.1 g of boric oxide, 260 g of N-lauroyl-L-phenylalanine, 62.5 g of 1-ethoxy-2-propanol and 153 g of n-dodecylamine were introduced to the flask, and the reaction was carried out for 10 hours under nitrogen atmosphere at 125° C. After the end of the reaction, 500 g of hot water, 400 g of ethyl acetate and 9.3 g of 95% sulfuric acid aqueous solution were added thereto to make an extraction with acid. Subsequently, 500 g of hot water, 38 g of 27% sodium hydroxide aqueous solution and 13 g of sodium chloride were added thereto to make an extraction with alkali. From the remaining organic layer, the solvent was removed by distillation under reduced pressure and the resulting solid material was dried under reduced pressure to obtain the reaction product (343 g). A purity of the thus obtained N-lauroyl-L-phenylalanine-n-dodecyl amide was 96% in the determination of the purity by HPLC.

EXAMPLE 6

A 2L-flask equipped with a stirrer, an H-shaped tube having a device for reflux, a dropping instrument and a thermometer was arranged for a reactor and air in the reactor was replaced by nitrogen gas. 52.2 g of boric oxide, 235 g of N-palmitoyl glycine, 480 g of toluene, 111.1 g of 1-butanol and 95 g of di-n-propylamine were introduced to the flask, and a reaction for azeotropic (hylotropic) dehydration was conducted under nitrogen atmosphere for 18 hours to remove the water produced by heating the mixture under reflux.

After the end of the reaction, the reaction mixture was treated in the same steps and operations as those in the example 1, and then the material in liquid form obtained after removal of the solvent was cooled while stirring to prepare granulated solid material. The material was collected by filtration and dried under reduced pressure to obtain the reaction product (267 g). A purity of the obtained N-palmitoyl glycine-N',N'-di-n-propyl amide was 98% in the determination of the purity by HPLC.

EXAMPLE 7

A 2L-flask equipped with a stirrer, an H-shaped tube having a device for reflux, a dropping instrument and a thermometer was arranged for a reactor and air in the reactor was replaced by nitrogen gas. 52.2 g of boric oxide, 247 g of N-lauroyl-L-glutamic acid ("AMISOFT LA", manufactured by Ajinomoto Co., Inc.), 480 g of toluene, 111.1 g of 1-butanol and 159.7 g of piperidine were introduced to the flask, and a reaction for azeotropic dehydration was conducted under nitrogen atmosphere for 20 hours to remove the water produced by heating the mixture under reflux.

After the end of the reaction, 600 g of water and 200 g of diethyl ether were added thereto, and then 18.6 g of 95% sulfuric acid aqueous solution was added thereto to prepare two phases (layers) in the solution and separate them, and then the water phase was removed. Further, 600 g of 1% sulfuric acid aqueous solution was added to the remaining organic layer, and then a step for extraction with an acid was effected. Subsequently, by adding 600 g of water and 75 g of 27% sodium hydroxide aqueous solution thereto, the step for extraction with an alkali was conducted repeatedly twice. The remaining organic layer was washed with sodium chloride aqueous solution, and the water in the organic solvent was removed with anhydrous sodium sulfate, and then the solvent was removed by distillation under reduced pressure. The resulting material was dried to obtain the reaction product (320g). A purity of the obtained N-lauroyl-L-glutamic acid di-piperidyl amide was 95% in the determination of the purity by HPLC.

COMPARATIVE EXAMPLE 1

A 2L-flask equipped with a stirrer, an H-shaped tube having a device for reflux, a dropping instrument and a thermometer was arranged for a reactor and air in the reactor was replaced by nitrogen gas. 52.2 g of boric oxide, 247 g of N-lauroyl-L-glutamic acid ("AMISOFT LA", manufactured by Ajinomoto Co., Inc.), 480 g of toluene and 137.2 g of n-butylamine were introduced to the flask, and a reaction for azeotropic dehydration was conducted under nitrogen atmosphere for 10 hours to remove the water produced by heating the mixture under reflux.

A state of progress of the reaction was confirmed through the HPLC, and as a result, it was found that a main product was a mono-amide derivative and a di-amide derivative as the objective compound was slightly produced. The step and operation for treatment were conducted in the same manner as those in the example 1 until the step for extraction with an acid. The organic solvent was removed by the azeotropic distillation, and the resulting material was dried under reduced pressure to obtain the reaction mixture (291 g). A purity of the obtained N-lauroyl-L-glutamic acid di-n-butyl amide was 28% in the determination of the purity by HPLC.

COMPARATIVE EXAMPLE 2

A 2L-flask equipped with a stirrer, an H-shaped tube having a device for reflux, a dropping instrument and a thermometer was arranged for a reactor and air in the reactor was replaced by nitrogen gas. 52.2 g of boric oxide, 247 g of N-lauroyl-L-glutamic acid ("AMISOFT LA", manufactured by Ajinomoto Co., Inc.), 480 g of toluene and 159.7 g of piperidine were introduced to the flask, and a reaction for azeotropic dehydration was conducted under nitrogen atmosphere for 20 hours to remove the water produced by heating the mixture under reflux.

A state of progress of the reaction was confirmed through the HPLC, and as a result, it was found that a main product was a mono-amide derivative and a di-amide derivative as the objective compound was slightly produced. The step and operation for treatment were conducted in the same manner as those in the example 7 until the step for extraction with an acid. The resulting organic layer was washed with sodium chloride aqueous solution, and then the water in the organic solvent was removed with anhydrous sodium sulfate, and then the solvent was removed by distillation under reduced pressure. The resulting material was dried to obtain the reaction mixture (282 g). A purity of the obtained N-lauroyl-L-glutamic acid dipiperidyl amide was 8% in the determination of the purity by HPLC.

EFFECT OF INVENTION

According to the present invention, in a process for producing N-acyl amino acid amide comprising a condensation reaction of an N-acyl amino acid, which may be in the free form or in the salt form, with amine and/or ammonia, preferably a primary amine, a secondary amine and/or an ammonia under dehydration, said reaction is conducted (performed) in the presence of at least one boron compound as the catalyst under coexistence of at least one alcohol as the auxiliary (assistant) solvent whereby the desired and objective product of N-acyl amino acid amide can be obtained at a higher yield for a shorter time, in comparison with the process without the coexistence of the auxiliary solvent.

What is claimed is:

1. In a process for producing N-acyl amino acid amide comprising a condensation reaction of N-acyl amino acid or the salt thereof with amine and/or ammonia under dehydrating conditions, an improved process wherein said condensation reaction is conducted in the presence of boron compound as the catalyst with alcohol coexistent as the auxiliary solvent.

2. The process according to claim 1, wherein said amine is one or more compounds selected from the group consisting of straight chain, branched chain, saturated, unsaturated, monoalcohol, di-alcohol, aromatic, alicyclic primary, and secondary amines having 1 to 60 carbon atoms.

3. The process according to claim 1, wherein said boron compound as the catalyst used is one or more compounds selected from the group consisting of orthoboric acid, metaboric acid, pyroboric acid and boric oxide.

4. The process according to claim 1, wherein said alcohol used as the auxiliary solvent is one or more compounds selected from the group consisting of straight chain or branched chain, saturated or unsaturated aliphatic alcohol having 3 to 8 carbon atoms, saturated or unsaturated cyclic alcohol having 3 to 8 carbon atoms and saturated or unsaturated alkyl ether alcohol.

5. The process according to claim 4, wherein said saturated or unsaturated alkyl ether alcohol is at least one compound selected from the compounds represented by the following general formula (1):

$$R^1\text{—}O\text{—}R^2\text{—}OH \qquad (1)$$

wherein $R^1$ denotes a straight chain or branched chain, alkyl group or unsaturated hydrocarbon radical having 1 to 4 carbon atoms, and $R^2$ denotes a straight chain or branched chain alkyl group having 2 to 5 carbon atoms.

6. The process according to claim 1, wherein said condensation reaction is conducted at a temperature of 98 to 150° C.

7. The process according to claim 1, wherein said condensation reaction is conducted in a medium comprising one or more alcohols as the auxiliary solvent.

8. The process according to claim 7, wherein the said medium further comprises a medium for the removal of water by azeotropic distillation.

9. The process according to claim 1, wherein said condensation reaction is conducted under acidic conditions.

10. A process for producing N-acyl amino acid amide, comprising a condensation reaction of N-acyl amino acid or the salt thereof with one or more compounds of primary amine, secondary amine and ammonia under dehydrating conditions in the presence of a boron compound as the catalyst with at least one alcohol coexistent as the auxiliary solvent.

11. The process according to claim 1, wherein the amino acid component of said N-acyl amino acid or salt thereof is selected from the group consisting of an acidic amino acid, a neutral amino acid, a basic amino acid, an α-amino acid, a β-amino acid, and a γ-amino acid.

12. The process according to claim 1, wherein the amino acid component of said N-acyl amino acid or salt thereof is selected from the group consisting of glycine, β-alanine, α-alanine, valine, leucine, phenylalanine, 3,4-dioxyphenylalanine, serine, threonine, methionine, lysine, ornithine, arginine, histidine, ε-aminocaproic acid, glutamic acid, and aspartic acid.

13. The process according to claim 1, wherein the acyl group of said N-acyl amino acid or salt thereof is derived from the group consisting of a straight chain, a branched chain, a saturated fatty acid, an unsaturated fatty acid, and an aromatic carboxylic acid having 1–30 carbon atoms.

14. The process according to claim 1, wherein the acyl group of said N-acyl amino acid or salt thereof is selected from the group consisting of formyl, acetyl, propionyl, caproyl, capryloyl, caprinoyl, lauroyl, myristoyl, palmitoyl, stearoyl, behenoyl, oleoyl, linoleoyl, coconut oil fatty acid, hardened beef tallow fatty acid, and benzoic acid.

15. The process according to claim 1, wherein said N-acyl amino acid or salt thereof is selected from the group consisting of N-lauroyl-L-glutamic acid, N-palmitoyl-L-valine, N-laroyl-L-phenyalanine, and N-palmitoyl-glycine.

16. The process according to claim 1, wherein said amine is selected from the group consisting of methylamine, ethylamine, propylamine, butylamine, hexylamine, octylamine, 2-ethylhexylamine, laurylamine, cetylamine, stearylamine, cycopentylamine, cyclohexylamine, 4-isopropylcyclohexylamine, aniline, benzylamine, naphthylamine, 4-isopropylaniline, dimethylamine, N-methylethylamine, diethylamine, di-n-propylamine, di-n-butylamine, N-methylbutylamine, piperidine, 3,5-dimethylpiperidine, N-methyldodecylamine, dilaurylamine, distearylamine, N-methylbenzylamine, monoethanolamine, and diethanolamine.

17. The process according to claim 1, wherein said amine is selected from the group consisting of n-butylamine, n-octylamine, n-dodecylamine, di-n-propylamine, and piperidine.

18. The process according to claim 1, wherein said boron compound as the catalyst used is selected from the group consisting of the neutralized form of borate, borax, and ammonium borate.

19. The process according to claim 1, wherein said boron compound as the catalyst used is selected from the group consisting of boric oxide and borax.

20. The process according to claim 1, wherein said alcohol used as the auxiliary solvent is selected from the group consisting of 1-propanol, 2-propanol, 1-butanol, 2-butanol, 2-methyl-1-propanol, tert-butanol, 1-pentanol, 2-methyl-1-butanol, 4-methyl-1-butanol, 2-methyl-2-butanol, 1-hexanol, 1-heptanol, 1-octanol, 2-ethylhexanol, allyl alcohol, crotyl alcohol, methylvinyl carbinol, cyclopentanol, and cyclohexanol.

21. The process according to claim 1, wherein said alcohol used as the auxiliary solvent is selected from the group consisting of 2-methoxy ethanol, 2-ethoxy ethanol, 2-propoxy ethanol, 2-isopropoxy ethanol, 2-butoxy ethanol, 1-methoxy-2-propanol, 1-ethoxy-2-propanol, 3-ethoxy-1-propanol, 1-propoxy-2-propanol, 1-tert-butoxy-2-propanol, 1-methoxy-2-butanol, 3-methoxy-1-butanol, 3-methoxy-3-methyl-1-butanol, ethylene glycol vinyl ether, ethylene glycol allyl ether, propylene glycol vinyl ether, and propylene glycol allyl ether.

22. The process according to claim 1, wherein said alcohol used as the auxiliary solvent is selected from the group consisting of 1-butanol and 1-ethoxy-2-propanol.

23. The process according to claim 1, wherein 1.0 to 3.0 equivalents of said amine is used per carboxyl group of said N-acyl amino acid.

24. The process according to claim 1, wherein 1.0 to 1.5 equivalents of said amine is used per carboxyl group of said N-acyl amino acid.

25. The process according to claim 1, wherein 0.1 to 10.0 equivalents of said boron compound is used per carboxyl group of said N-acyl amino acid.

26. The process according to claim 1, wherein said condensation reaction is conducted at a temperature of 110 to 150° C.

27. The process according to claim 1, wherein said condensation reaction is conducted at a temperature of 110 to 125° C.

28. The process according to claim 8, wherein the said azeotropic medium is selected from the group consisting of heptane, isooctane, methylcyclohexane, cycloheptane, methylcyclohexene, diisobutylene, toluene, xylene, octane, octene, dimethylcyclohexane, and trimethylcyclohexane.

29. The process according to claim 8, wherein said azeotropic medium is toluene.

* * * * *

UNITED STATES PATENT AND TRADEMARK OFFICE
CERTIFICATE OF CORRECTION

PATENT NO. : 6,335,468 B1
DATED : January 1, 2002
INVENTOR(S) : Toshihiko Hatajima et al.

It is certified that error appears in the above-identified patent and that said Letters Patent is hereby corrected as shown below:

Column 5,
Line 21, "2-methyl-i-propanol"; should read -- 2-methyl-1-propanol --

Column 6,
Line 4, "buidup"; should read -- build-up --

Column 7,
Lines 45 and 46, add -- is desired. --; Begin line 46 with -- That is, --

Column 8,
Line 12, "8"; should read -- (s) --

Signed and Sealed this

Nineteenth Day of November, 2002

Attest:

JAMES E. ROGAN
Attesting Officer    Director of the United States Patent and Trademark Office